United States Patent [19]

Shturman

[11] Patent Number: 5,190,046
[45] Date of Patent: Mar. 2, 1993

[54] ULTRASOUND IMAGING BALLOON CATHETER

[75] Inventor: Leonid Shturman, Minneapolis, Minn.

[73] Assignee: Shturman Cardiology Systems, Inc., Minneapolis, Minn.

[21] Appl. No.: 877,469

[22] Filed: May 1, 1992

[51] Int. Cl.⁵ .............................................. A61B 8/12
[52] U.S. Cl. .......................... 128/662.06; 128/660.03; 604/96
[58] Field of Search ............... 128/660.03, 662.06; 604/96–103; 606/159

[56] References Cited

U.S. PATENT DOCUMENTS

| | | | |
|---|---|---|---|
| Re. 33,569 | 4/1991 | Gifford, III et al. | 606/159 |
| 4,669,469 | 6/1987 | Gifford, III et al. | 128/305 |
| 4,748,982 | 6/1988 | Horzewski et al. | 128/344 |
| 4,771,774 | 9/1988 | Simpson et al. | 128/305 |
| 4,781,186 | 11/1988 | Simpson et al. | 128/305 |
| 4,794,931 | 1/1989 | Yock | 128/680.03 |
| 4,911,170 | 3/1990 | Thomas, III et al. | 128/660.03 X |
| 4,917,097 | 4/1990 | Proudian et al. | 128/662.06 |
| 4,979,951 | 12/1990 | Simpson | 606/159 |
| 5,000,185 | 3/1991 | Yock | 128/662.03 |
| 5,010,886 | 4/1991 | Passafaro et al. | 128/660.03 |
| 5,029,588 | 7/1991 | Yock et al. | 128/660.03 X |
| 5,095,911 | 3/1992 | Pomeranz | 128/662.06 X |
| 5,100,424 | 3/1992 | Jang et al. | 128/662.06 X |
| 5,115,814 | 5/1992 | Griffith et al. | 128/660.03 X |

FOREIGN PATENT DOCUMENTS

| | | |
|---|---|---|
| 9101813 | 3/1991 | PCT Int'l Appl. |
| 9101815 | 3/1991 | PCT Int'l Appl. |
| 9103365 | 5/1991 | PCT Int'l Appl. |
| 9103521 | 5/1991 | PCT Int'l Appl. |

OTHER PUBLICATIONS

Bom, N., et al., "Early and Recent Intraluminal Ultrasound Devices," *International Journal of Cardiac Imaging*, 4:79–88, 1989.

Utsugi, M. "UTS Diagnostic Apparatus for Coeliac Examination", Europ. Pat. Appln No. 0062315 published Oct. 1982.

Hisanaga, K. et al., "A New Transesophageal Real-Time Linear Scanner and Initial Clinical Results", p. 112, Proc. 23rd AIUM 1978.

*Primary Examiner*—Francis Jaworski
*Attorney, Agent, or Firm*—Gregory P. Kaihoi

[57] ABSTRACT

An ultrasound imaging balloon catheter for imaging near a wall of a cavity or passageway. The apparatus includes an elongated catheter having a primary lumen with a distal opening enveloped by the balloon. A preshaped ultrasound catheter carrying ultrasound transducer elements can be advanced through the catheter and inserted into the inflated balloon. The shape of the distal portion of the ultrasound catheter positions the ultrasound transducer elements radially outwardly of the catheter lumen, and preferably adjacent to the wall of the balloon, thus centering the image close to the wall of the cavity or passageway, giving greater depth of image at the portion of the wall of interest.

13 Claims, 13 Drawing Sheets

ULTRASOUND IMAGING BALLOON CATHETER

FIELD OF THE INVENTION

The invention relates to balloon catheters insertable into bodily passageways and cavities, and more particularly to such a balloon catheter having ultrasound imaging capabilities.

BACKGROUND OF THE INVENTION

Catheters incorporating ultrasound imaging capabilities have been utilized for a number of years for gaining information about the internal condition of the human body. See, e.g., N. Bom, *Early and Recent Intraluminal Ultrasound Devices*, Int'l J. of Card. Imag., 4:79–88 (1989), reprinted in N. Bom, *Intravascular Ultrasound* (Kluwer Academic Publishers, 1989). Such imaging catheters, e.g., have been used to image areas in and around arteries, the heart, urinary tract, esophagus, large intestine, and other areas. In arterial (and other small diameter) applications, both the catheter and the ultrasound transducer elements of necessity must be very small in size, resulting in limited resolution and range (or "depth") of the resulting image.

Moreover, in some percutaneous procedures, the diameter of the catheter or similar instrument being used is not so much limited by the diameter of the area of interest (e.g., the aorta) as it is by the diameter of the entry passageway (such as the femoral artery); hence, at the area of interest the diameter of the instrument may be significantly smaller than the diameter of the passageway or cavity, exacerbating the problems resulting from the limited imaging range of the small diameter ultrasound transducer apparatus.

SUMMARY OF THE INVENTION

The invention provides an ultrasound imaging balloon catheter apparatus for positioning an ultrasound transducer closer to a wall of a bodily passageway or cavity than possible with conventional imaging apparatus, thus centering the image closer to the wall of the cavity or passageway and increasing the depth of the ultrasonic image of tissue surrounding the cavity or passageway of interest.

The apparatus of the invention includes an elongated balloon-carrying catheter having an elongated inner lumen in communication with an inflatable balloon through a specially shaped distal opening located in the distal end portion of the catheter. The inflatable balloon is secured to the catheter covering and enveloping the above described specially shaped distal opening of the catheter. An ultrasound catheter is provided with ultrasound transducer means located in its distal end segment. The ultrasound catheter is preferably preformed so that, when the balloon is inflated, the distal end segment of the ultrasound catheter can be advanced out through the specially shaped distal opening in the balloon-carrying catheter and into the inflated balloon to locate the ultrasound transducer means radially outwardly of the lumen of the balloon-carrying catheter, preferably immediately adjacent the wall of the balloon which in turn preferably abuts the wall of the passageway/cavity of interest.

In a particularly preferred embodiment, the ultrasound catheter is pre-curved in a gentle "S"-shaped configuration so that the transducer elements remain oriented with respect to the surface of the wall of interest so as to yield an image which is a substantially perpendicular cross-section of the wall.

BEST MODE FOR CARRYING OUT THE INVENTION

Figure 1:
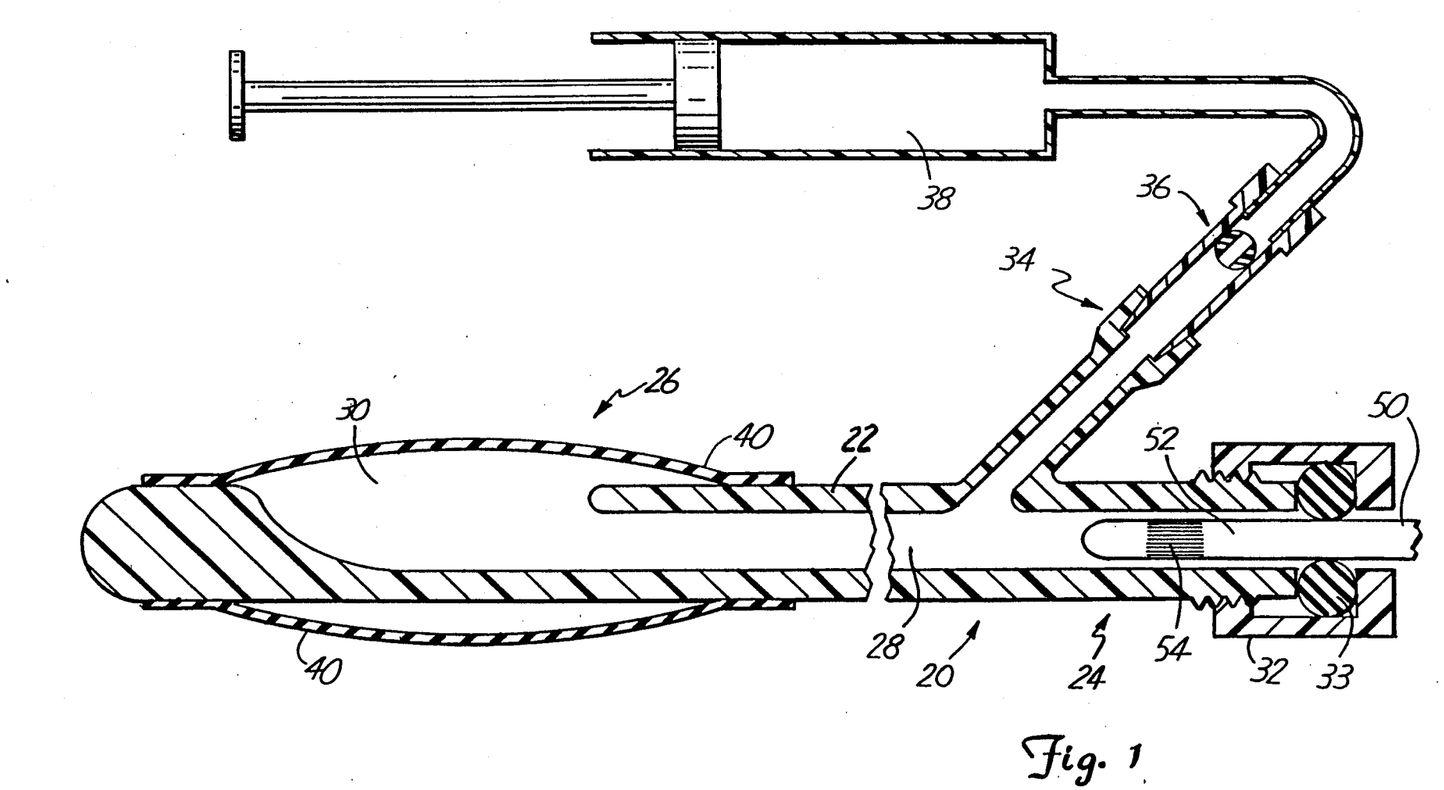
FIG. 1 is a cross-sectional view of the ultrasound imaging balloon catheter of the invention.

FIG. 1 shows in somewhat schematic fashion one embodiment of the ultrasound imaging balloon catheter of the invention. The balloon-carying catheter, designated generally as 20, includes an elongated shaft 22 having proximal and distal end portions 24 and 26, respectively, and an inner lumen 28 in communication with balloon 40 through a specially shaped distal opening 30. The specially shaped distal opening 30 is located in the distal end portion 26 of the catheter shaft 22 and is enveloped by the balloon 40. At the proximal end 24 of the balloon carrying catheter 20, an inflation port 34 is provided for connecting a syringe 38 (by way of a stop cock 36) for inflation of the balloon 40 (alternate inflation means may also be utilized).

Figure 13:
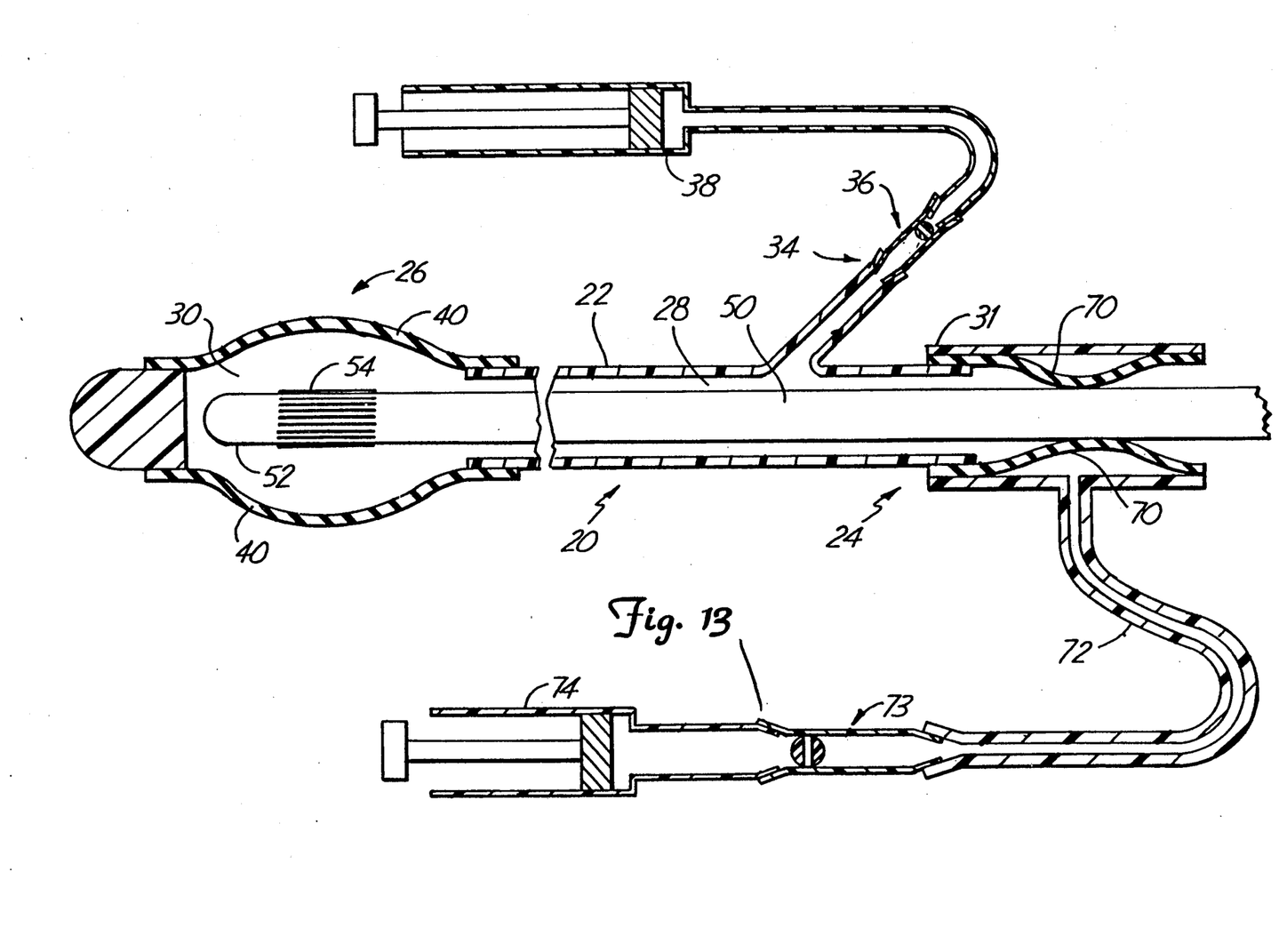
FIG. 13 is a cross-sectional view of an embodiment of the invention similar to FIG. 5 illustrating a structure for sealing the proximal end of the balloon catheter of the invention.

A proximal fitting 32, such as an O-ring seal 33 (or equivalent sealing means), is provided for allowing introduction of an ultrasound catheter 50 carrying a multi-element ultrasound transducer array 54 on its distal portion 52. An alternate sealing means is depicted in FIG. 13. In this configuration (which depicts only schematically the distal end portions of the balloon catheter 20 and ultrasound catheter 50), an alternate proximal fitting 31 is provided which carries a circumferential and inwardly expandable sealing balloon 70. The sealing balloon 70 is connected by way of tubing 72 and stopcock 73 to an inflation syringe 74. Thus, sealing pressure of the sealing balloon 70 on the shaft of the ultrasound catheter 50 (or a pushing shaft 44, as described below) can be controlled by the physician, and longitudinal movement of the ultrasound catheter 50 (or pushing shaft 44) is easily accommodated.

Figure 2:
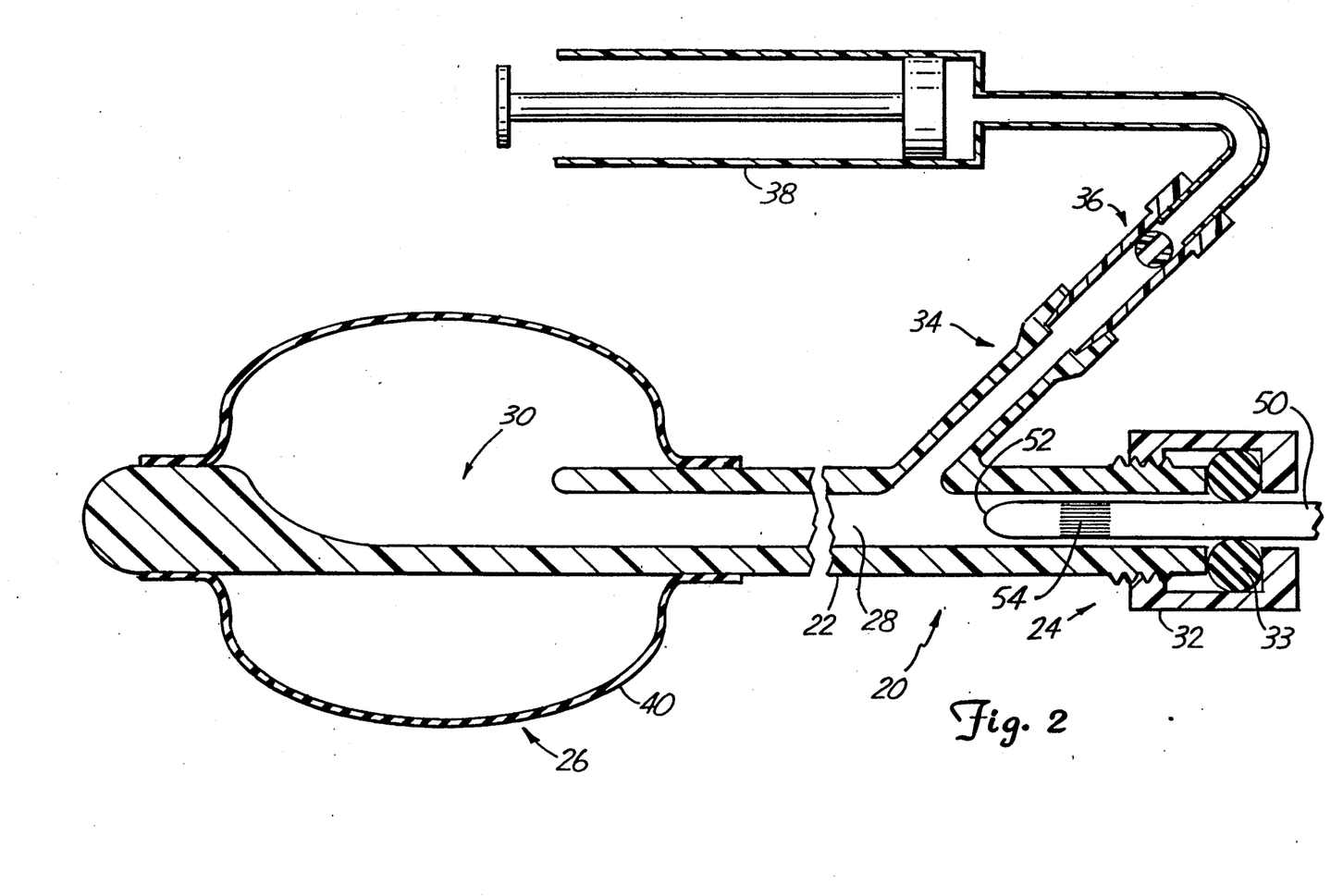
FIG. 2 is a cross-sectional view of the invention similar to FIG. 1 with the balloon inflated.
Figure 3:
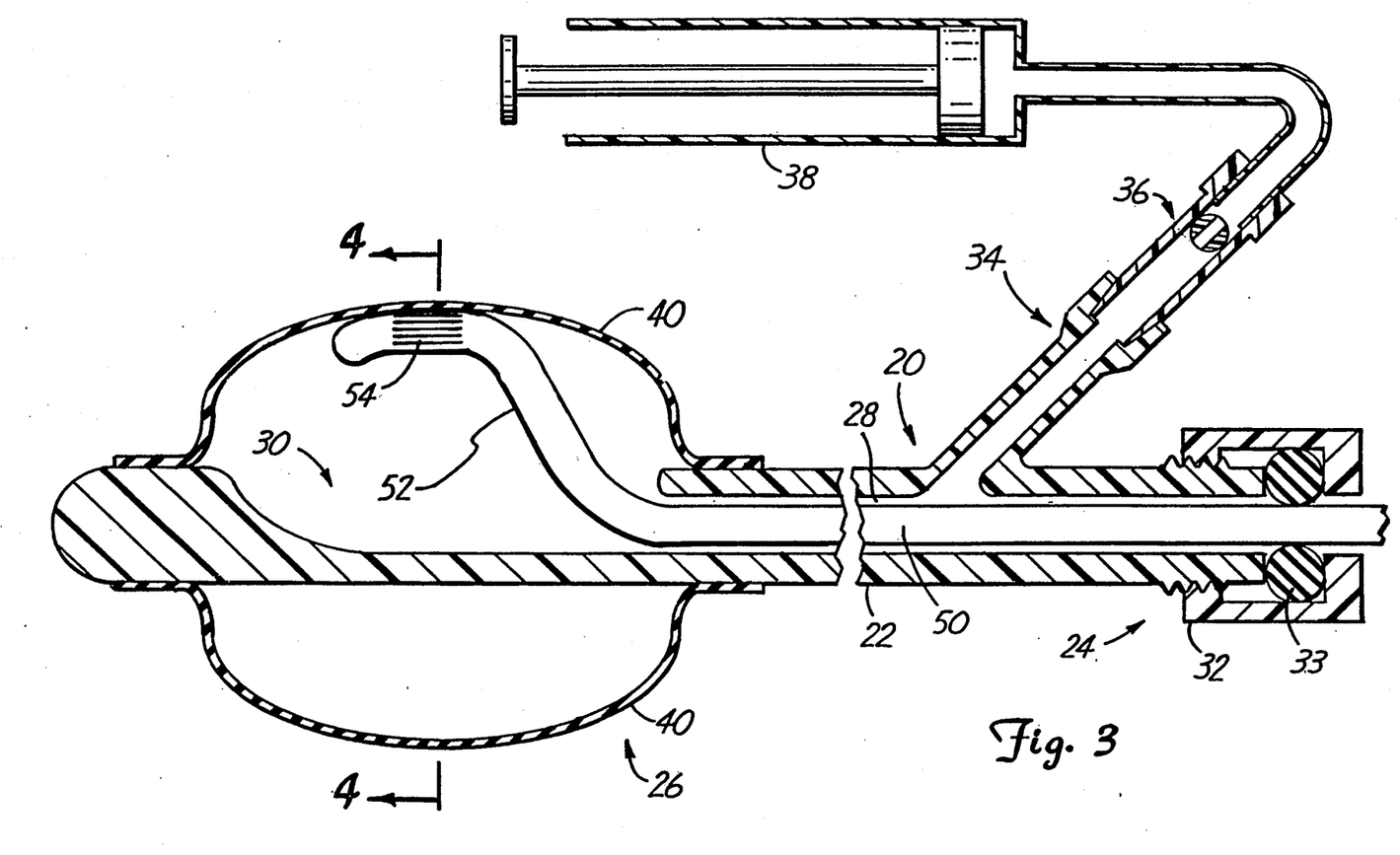
FIG. 3 is a cross-sectional view of the balloon catheter of the invention with the ultrasound catheter advanced into the balloon.

In FIG. 2, the syringe 38 has been actuated to inject sonolucent and preferably radio-opaque inflation fluid through the lumen 28 of the catheter 20 to at least partially inflate the balloon 40. The ultrasound catheter 50 would then be advanced through the lumen 28 of the catheter 20 until the distal portion 52 of the ultrasound catheter 50 enters the inflated balloon 40, as shown in FIG. 3. As illustrated in FIG. 3, the distal end portion 52 of the ultrasound catheter 50 preferably is flexible and pre-shaped so that as it passes out of the distal opening 30 in the catheter 20 and into the inflated balloon 40 this distal end portion 52 regains its original configuration, which locates the distal portion 52 carrying the ultrasound transducer array 54 radially outwardly of the catheter lumen 28. Preferably, the ultrasound transducer array 54 is located close to or immediately adjacent the wall of the balloon 40, which in turn will be located immediately adjacent to the wall of the passageway or cavity of interest. Thus, the area of interest being imaged will be much closer to the ultrasound transducer, giving greater depth of imaging of the tissue of interest.

Figure 4:
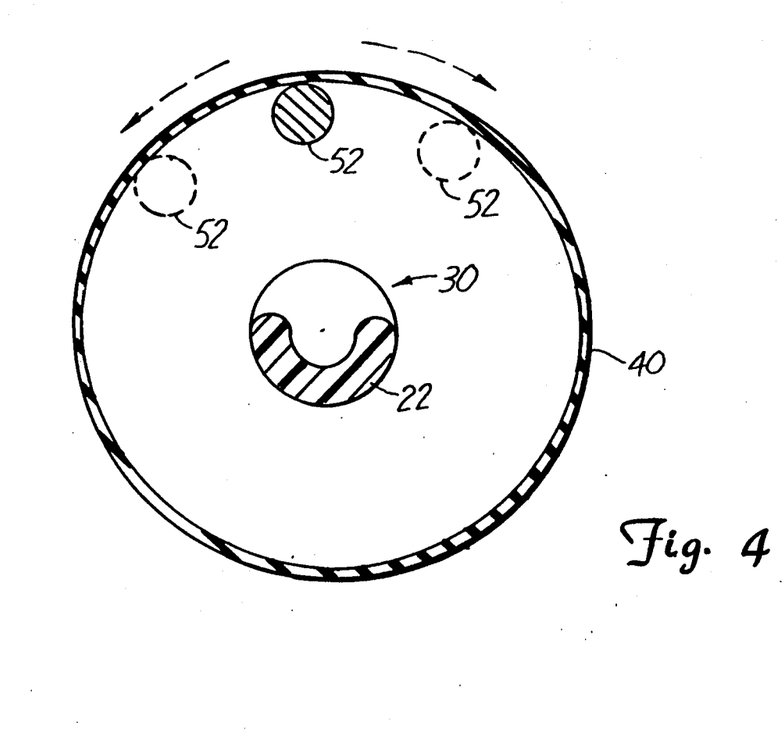
FIG. 4 is a cross-sectional view of FIG. 3 taken along line 4—4 thereof.
Figure 5:
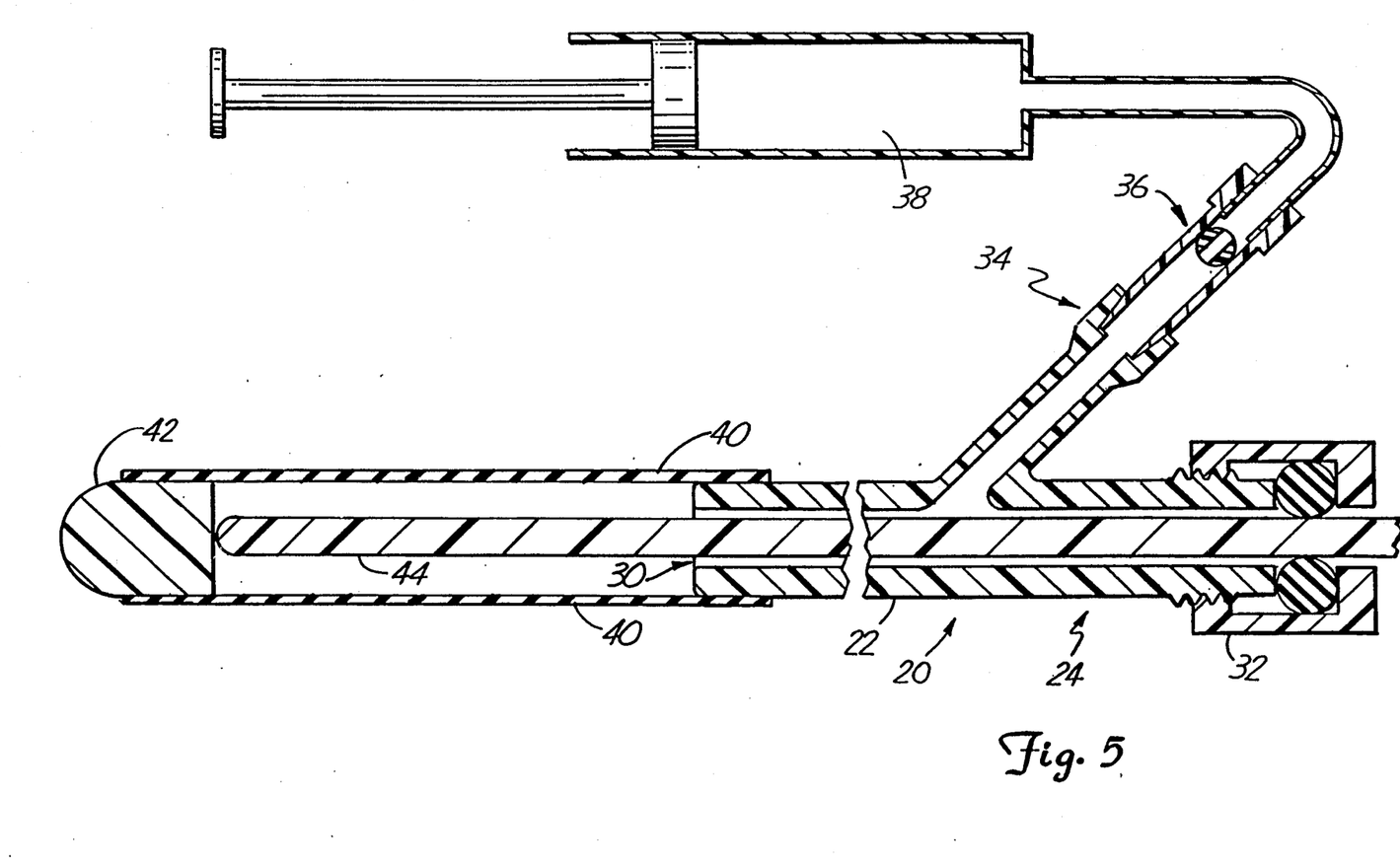
FIG. 5 is a cross-sectional view of an alternate embodiment of the ultrasound imaging balloon catheter of the invention.
Figure 6:
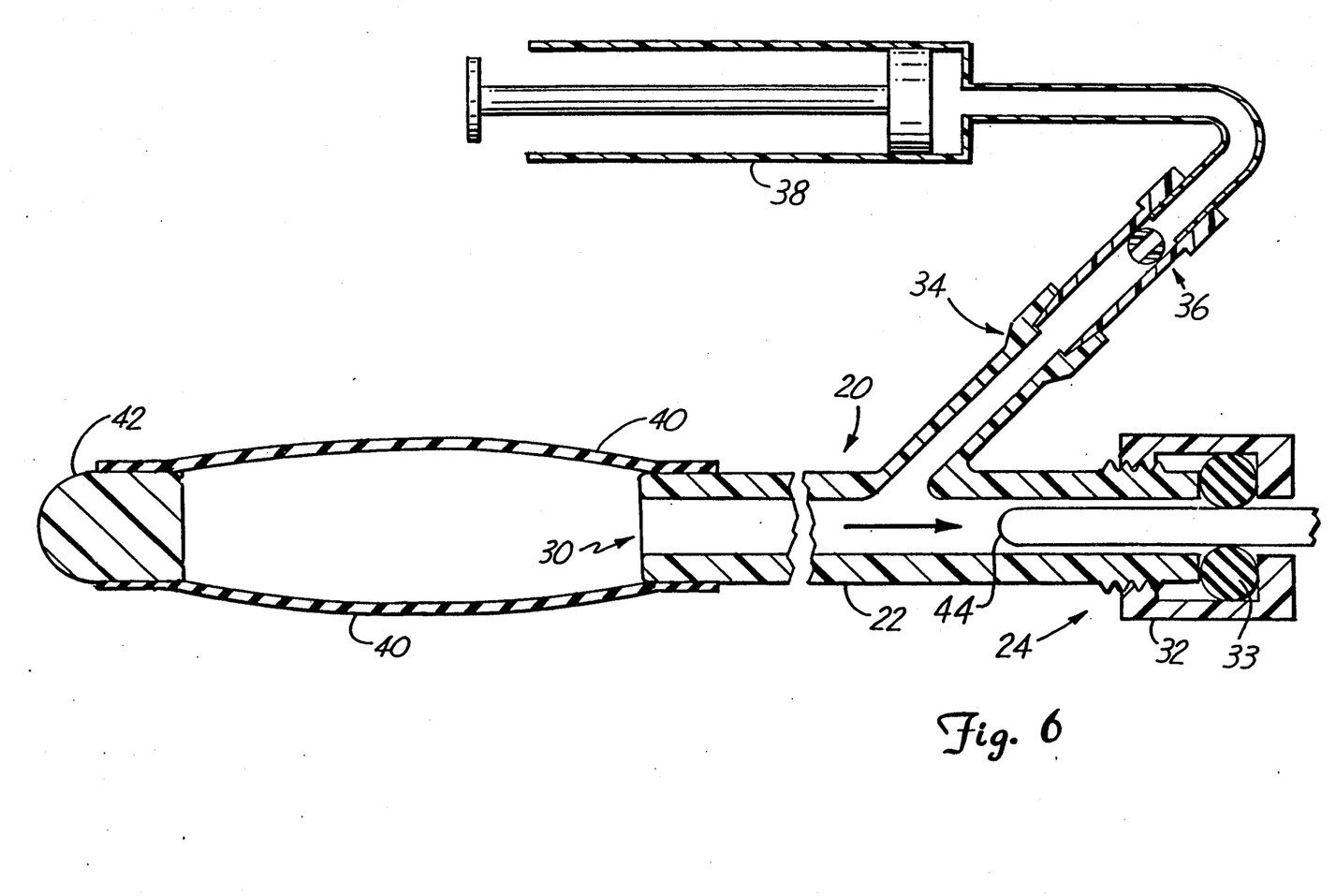
FIG. 6 is a cross-sectional view similar to FIG. 5 but with the balloon inflated and the pushing shaft being withdrawn.
Figure 7:
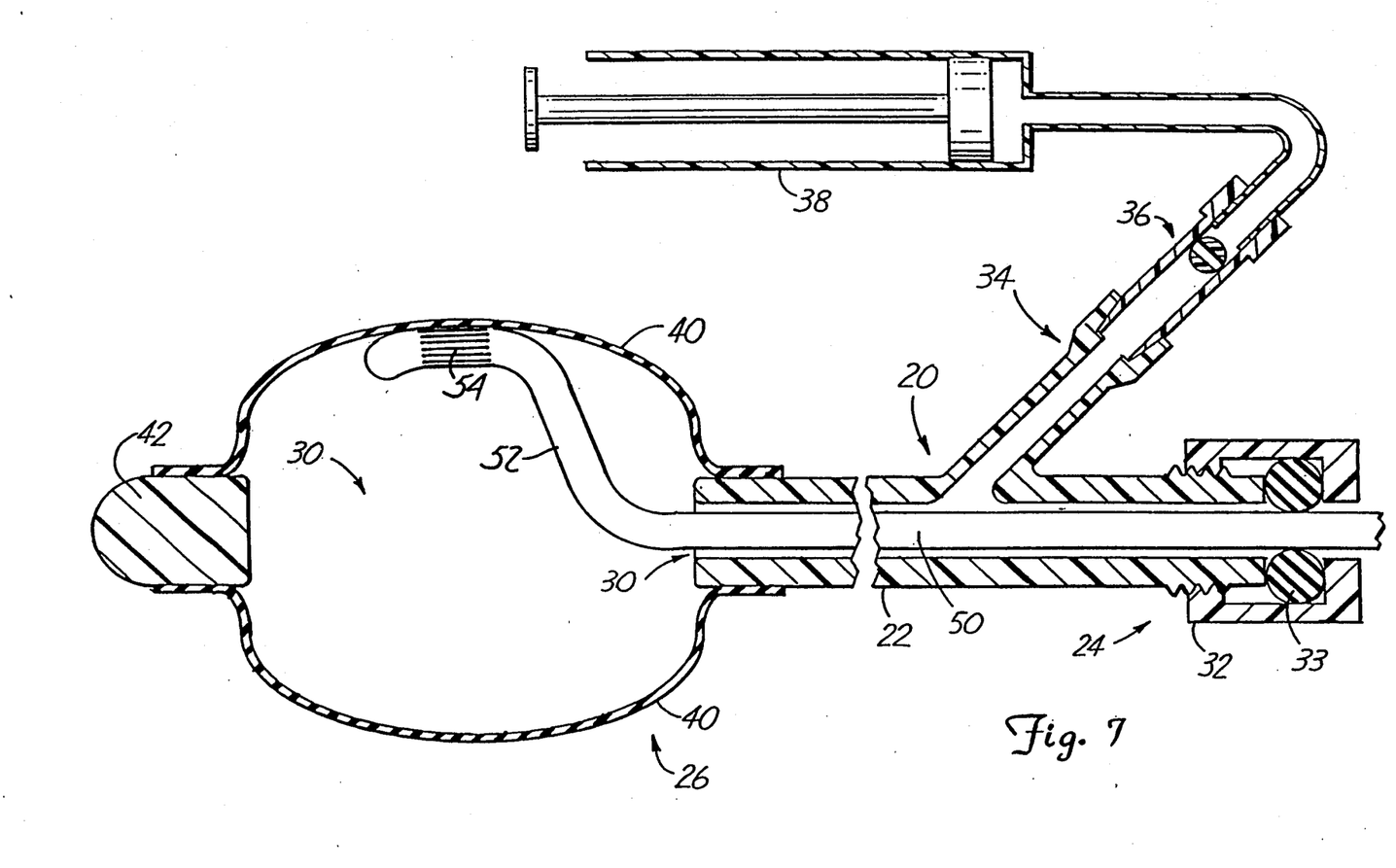
FIG. 7 is a cross-sectional view similar to FIG. 6 but with the ultrasound catheter advanced into the balloon.

When the distal opening 30 in the catheter 20 consists of a lateral opening in the catheter 20, as shown in FIGS. 1-3, the ultrasound catheter 50 and its distal portion 52 can be rotated through a limited range, as illustrated in FIG. 4. The arcuate range of motion of the distal portion 52 of the ultrasound catheter 50 is dictated by the circumferential extent of the lateral opening 30 in the shaft 22 of the balloon-carrying catheter 20. In an alternate embodiment depicted in FIG. 5, the distal opening 30 consists of the distal end of the elongated shaft 22 of the catheter 20. The balloon 40 extends from the distal end portion of the elongated shaft 22 to a relatively rigid distal tip 42, effectively making the distal opening 30 open 360° circumferentially about the catheter lumen 28. In this embodiment, a pushing shaft 44 is provided to give dimensional stability to the uninflated balloon so that the device can be advanced through a bodily passageway. Once the balloon is properly placed the balloon can be inflated and the pushing shaft can be removed, as shown in FIG. 6. The ultrasound catheter 50 can then be inserted into position, as illustrated in FIG. 7. The distal end segment 52 of the ultrasound catheter 50 can be rotated to any position desired to closely image any circumferential portion of the tissue beyond the wall of the balloon 40.

Figure 8:
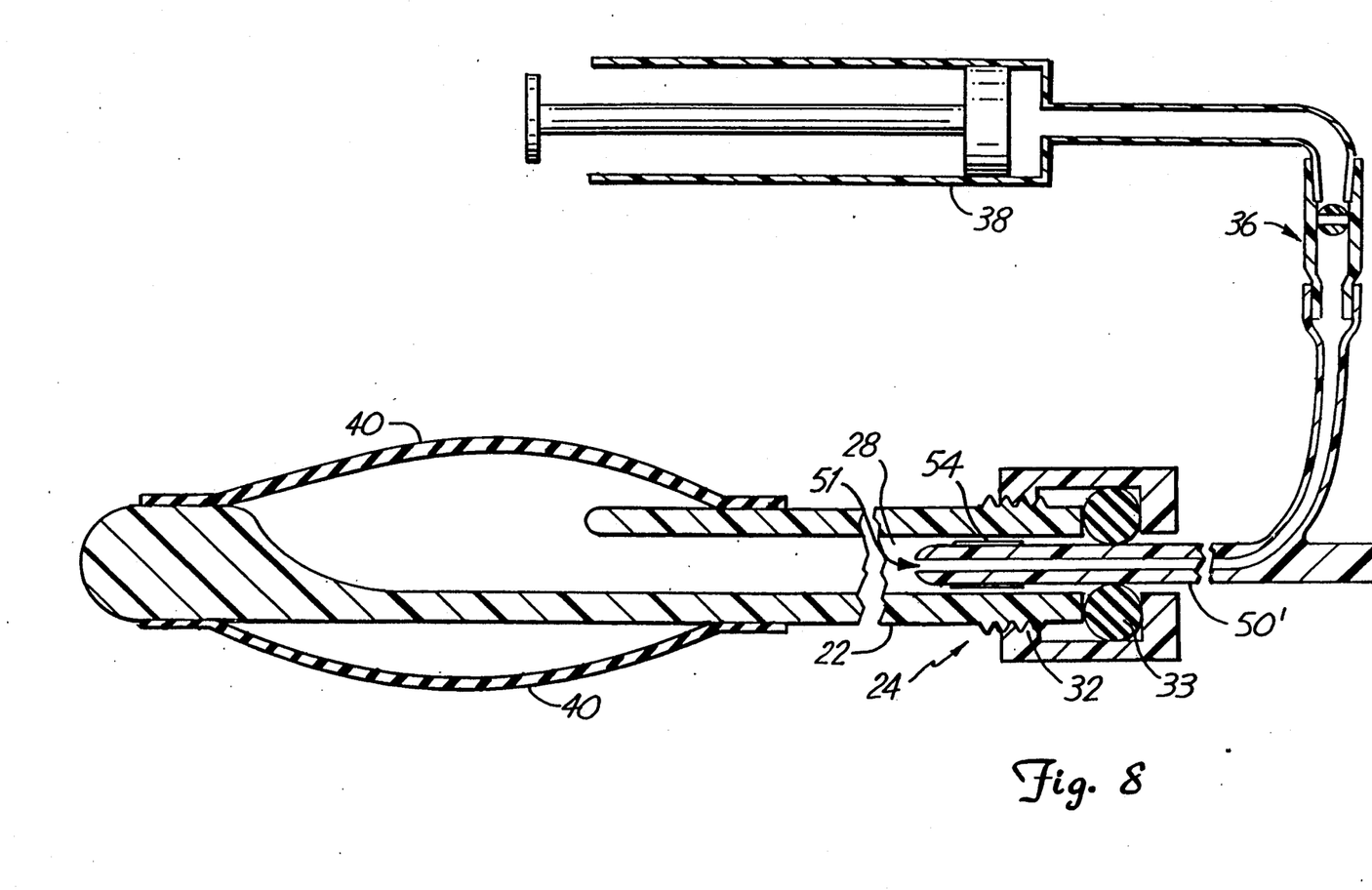
FIG. 8 is a cross-sectional view of an alternate embodiment of the ultrasound imaging balloon catheter of the invention.

FIG. 8 shows a slightly different embodiment of the invention wherein the ultrasound catheter 50' includes a lumen 51 through which ultrasound coupling fluid can be injected for inflating the balloon 40.

Figure 9:
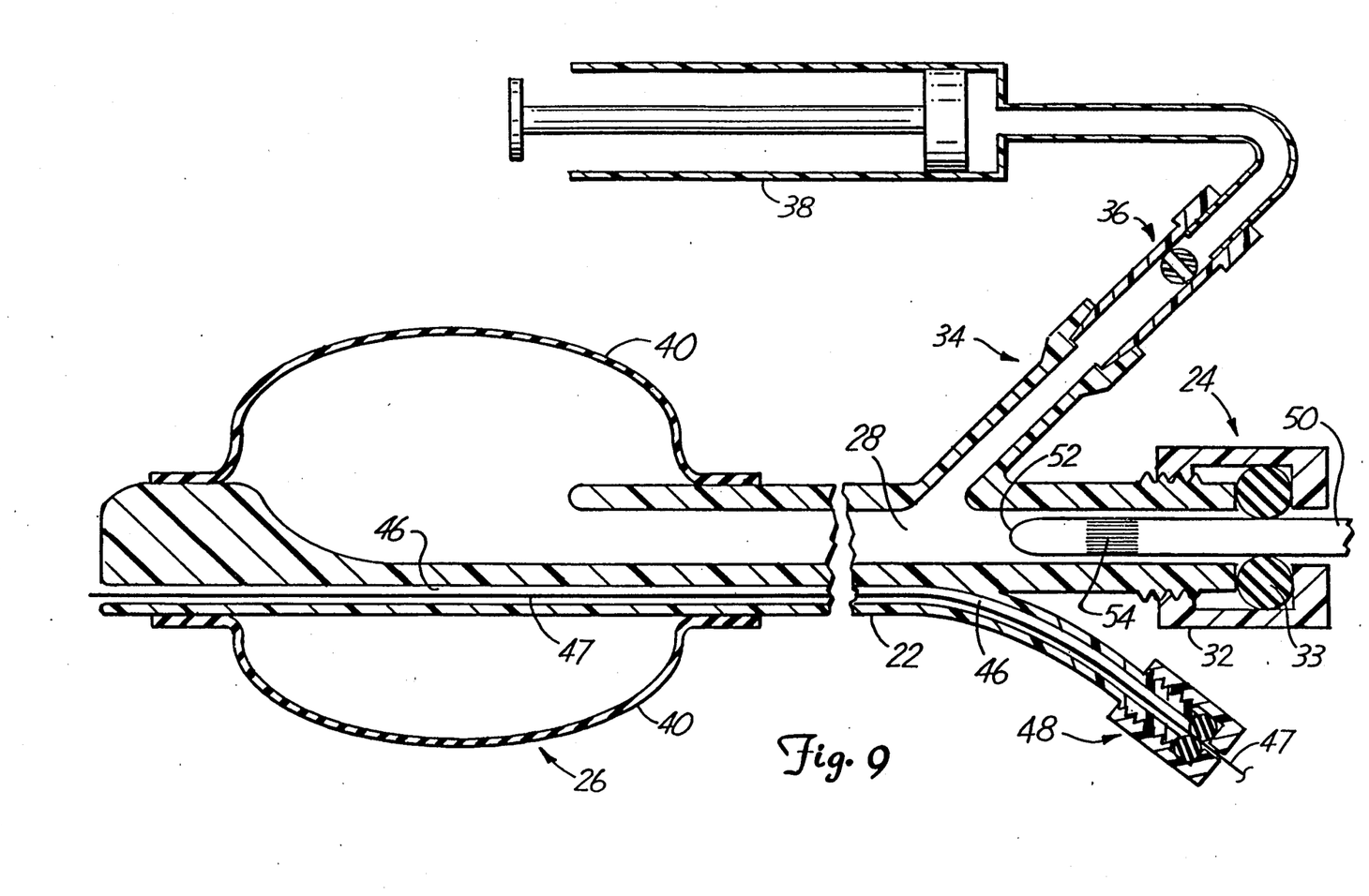
FIG. 9 is another embodiment of the ultrasound imaging balloon catheter of the invention incorporating a guide wire.

In many applications, it is desirable to utilize a guide wire to assist in accurate insertion and placement of the balloon catheter. To accommodate this, the embodiment shown in FIG. 9 includes a secondary lumen 46 extending through the entire length of the catheter 20 through which a guide wire 47 can be passed. A proximal fitting 48 is provided for introduction of the guide wire into the secondary lumen 46.

Figure 10:
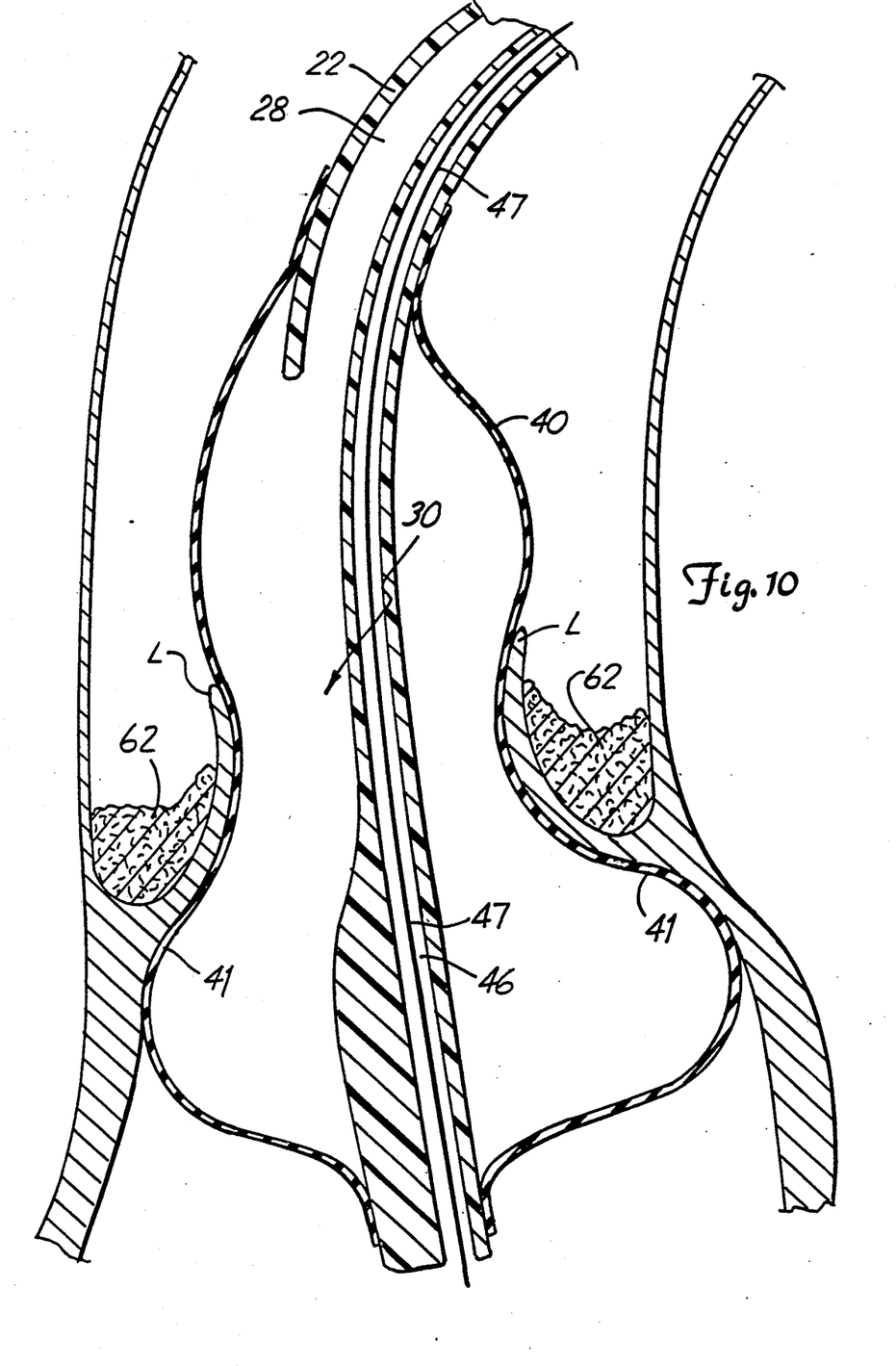
FIG. 10 is yet another embodiment of the invention as applied to imaging the aortic valve.
Figure 11:
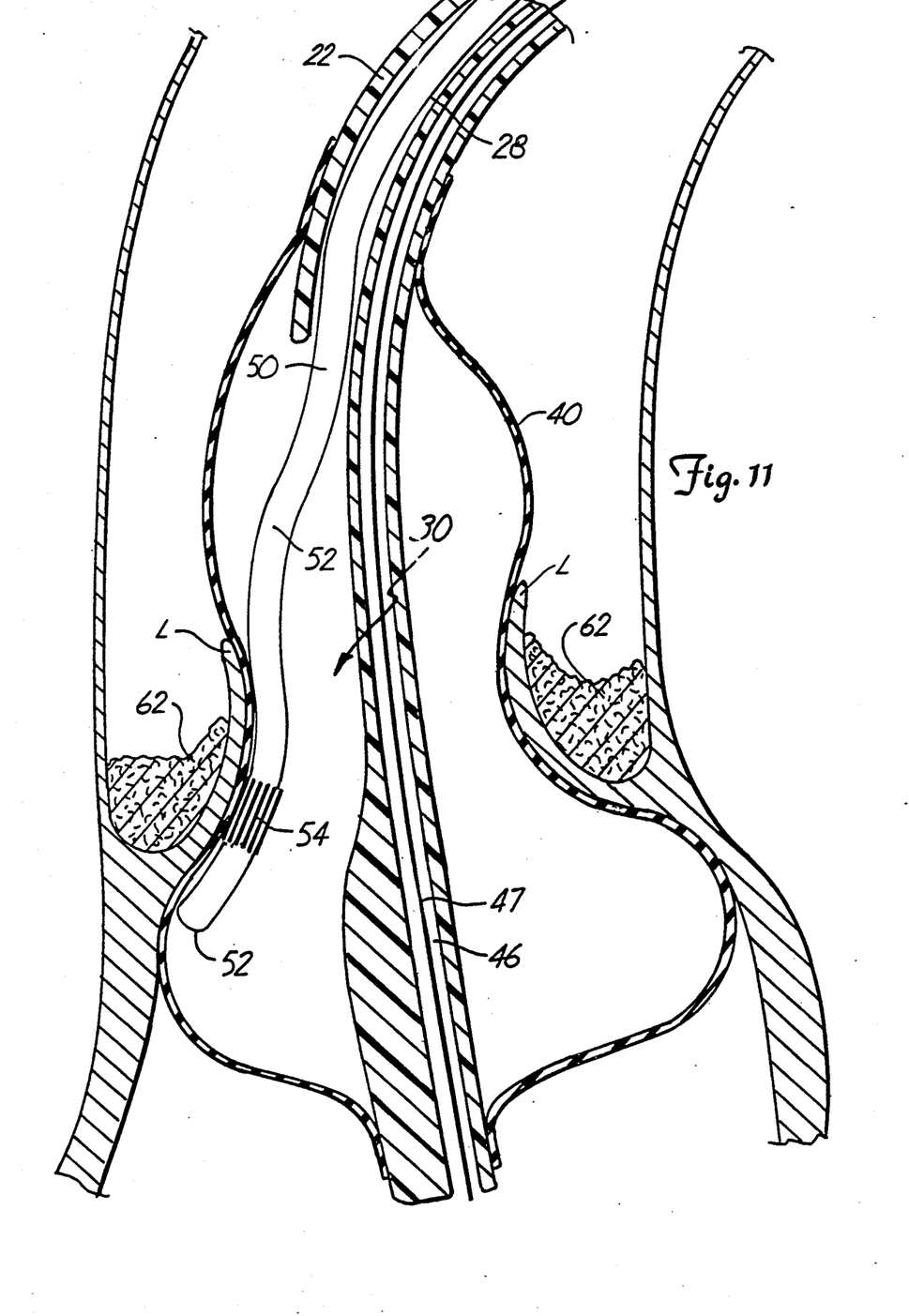
FIG. 11 is a cross-sectional view similar to FIG. 10 showing the ultrasound catheter inserted into position.
Figure 12:
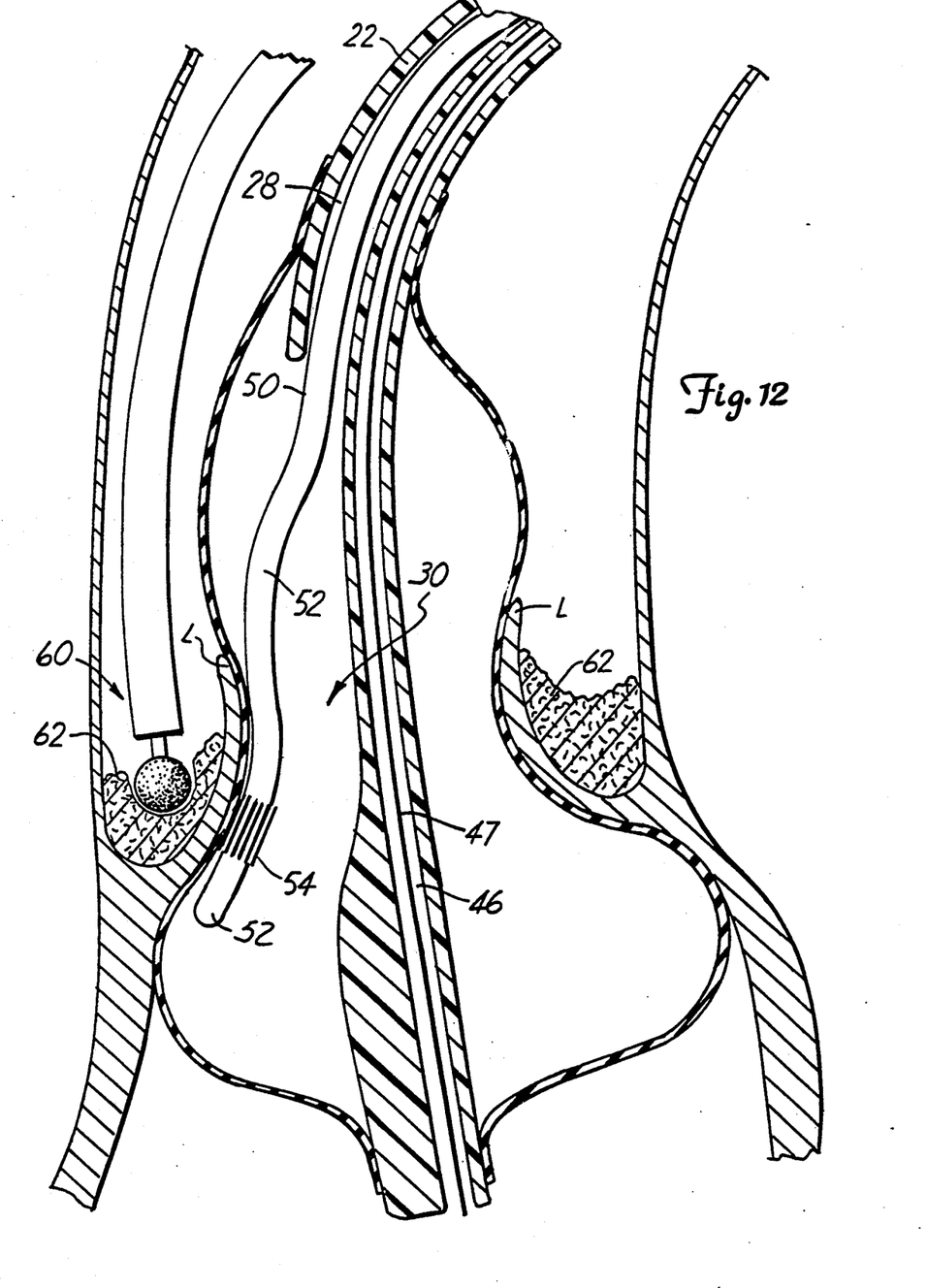
FIG. 12 is a view similar to FIGS. 10 and 11 demonstrating use of the ultrasound imaging balloon catheter in the removal of calcified deposits from a leaflet of the aortic valve.

FIGS. 10-12 illustrate one application of the ultrasound imaging balloon catheter of the invention. In my co-pending patent application Ser. No. 680,705, filed Apr. 4, 1991, entitled METHOD AND APPARATUS FOR IN VIVO HEART VALVE DECALCIFICATION, a method and apparatus is described for introducing an apparatus through the aorta across the aortic valve to remove calcified deposits from the superior (aortic) surface of the valve leaflets. In such an application of the present invention, the balloon 40 preferably is configured to include a shoulder 41 for engagement with the aortic valve to help position the balloon with respect to the valve leaflets "L". Once the balloon has been properly positioned, as shown in FIG. 10 (utilizing a guide wire 47), the ultrasound catheter 50 is introduced through the primary lumen 28 and positioned adjacent the wall of the balloon which abuts the valve leaflet L, providing a close image of the portion of the valve leaflet of interest. Notice in FIG. 11 that the ultrasound catheter 50 is pre-shaped so that the elements of the ultrasound transducer array 54 are generally parallel to the inferior (ventricular) surface of the valve leaflet L and the balloon 40 wall, rather than being parallel to the guide wire lumen 46. This provides for a cross-sectional image which is more closely perpendicular to the inferior (ventricular) surface of the aortic valve leaflet L. In FIG. 12, a decalcification tool 60 has been advanced and positioned to remove calcification deposits 62 from the valve leaflet L. In this application, the ultrasound transducer elements will provide an image to the physician indicating the relative thickness of the healthy (non-calcified) portion of the leaflet below the calcifications and the lower extent of the calcification deposits 62. Since such calcifications are generally opaque to ultrasound, the deposit removal tool generally will become ultrasonically identifiable just as it breaks through the calcifications.

The components of the ultrasound imaging balloon catheter of the invention can be made of any suitable materials. In particular, the catheter can be made of well known medical grade plastics, and the balloon similarly can be made from known materials such as latex, silicone, PET, and the like. The ultrasound transducer means can be of any suitable type, such as those commercially available from Cardiovascular Imaging Systems, Inc. (Sunnyvale, Calif.), Boston Scientific Corporation (Watertown, Mass.), Intertherapy Corporation (Santa Ana, Calif.) and Endosonics Corporation (Pleasanton, Calif.).

While a preferred embodiment of the present invention has been described, it should be understood that various changes, adaptations and modifications may be made therein without departing from the spirit of the invention and the scope of the appended claims.

What is claimed is:

1. An ultrasound imaging balloon catheter apparatus for use in positioning an ultrasound transducer near a wall of a cavity or passageway, comprising:

an elongated catheter having proximal and distal end portions and a tubular wall defining an inner lumen, the tubular wall including an opening in the distal end portion;

an inflatable balloon secured to the catheter and covering the opening in the distal end portion; and an ultrasound catheter having proximal and distal end segments and ultrasound transducer means carried in its distal end segment;

the distal opening in the tubular wall and the distal end segment of the ultrasound catheter being shaped and sized so that, when the balloon is inflated, the distal end segment of the ultrasound catheter including the ultrasound transducer means can be advanced through the distal opening into the balloon to locate the transducer means radially outwardly of the lumen of the elongated catheter.

2. The apparatus of claim 1 wherein the distal end segment of the ultrasound catheter is flexible and pre-curved so that when it exits the distal opening into the inflated balloon it assumes its pre-curved shape, positioning the ultrasound transducer means radially outwardly of the lumen of the elongated catheter.

3. The apparatus of claim 2 wherein the pre-curvature of the distal portion of the ultrasound catheter is generally S-shaped so that when it exits the distal opening into the inflated balloon it positions the ultrasound transducer means so as to provide a cross-sectional view generally perpendicular to the wall of the cavity or passageway being imaged.

4. The apparatus of claim wherein the distal opening comprises a lateral opening in the the tubular wall of the elongated catheter, such opening extending at least about one third of the way around such catheter.

5. The apparatus of claim wherein the distal opening comprises a distally open end of the tubular wall defining the catheter lumen, the balloon extending distally from such end of the tubular wall.

6. The apparatus of claim 5 wherein the balloon includes a generally rigid distal tip, the apparatus further including a pushing shaft removably receivable in the catheter lumen and being engagable against the generally rigid tip of the balloon to advance the catheter in the passageway or cavity.

7. The apparatus of claim I wherein the ultrasound catheter includes a lumen through which balloon inflation fluid can be introduced.

8. The apparatus of claim 1 wherein the catheter includes a secondary lumen through which a guide wire may be passed.

9. The apparatus of claim 1 wherein the balloon is shaped for engagement with and support of an aortic valve.

10. The apparatus of claim 1 wherein the elongated catheter includes a proximal opening through which the ultrasound catheter may be advanced into the lumen of the elongated catheter, the apparatus further including sealing means for sealing the proximal opening while allowing the ultrasound catheter to be advanced and retracted in the catheter lumen.

11. The apparatus of claim 10 wherein the sealing means comprises a generally cylindrical fitting and an inwardly expandable inflatable balloon carried by the fitting.

12. An ultrasound imaging balloon catheter apparatus for imaging near a wall of a cavity or passageway, comprising:
an elongated catheter having proximal and distal ends and a tubular wall defining primary and secondary inner lumens, the tubular wall of the primary lumen including a lateral opening near the distal end of the catheter, such opening extending at least about one third of the way around such catheter;
an inflatable balloon secured to the catheter near its distal end covering the lateral opening in the tubular wall;
inflation means for selectively inflating the balloon;
a guide wire slidably disposed in the secondary lumen of the catheter; and
a flexible ultrasound catheter having proximal and distal ends and ultrasound transducer means carried near its distal end;
the lateral opening in the tubular wall and a portion of the ultrasound catheter near its distal end being shaped, sized and pre-curved so that, when the balloon is inflated, the distal end of the ultrasound catheter including the ultrasound transducer means can be advanced through the opening in the tubular wall into the balloon, such distal end portion then assuming its pre-curved shape and thus positioning the ultrasound transducer means radially outwardly of the tubular wall and closer to the wall of the passageway or cavity than the catheter lumen.

13. A method of imaging a wall of a bodily cavity or passageway, comprising:
inserting into the passageway a balloon catheter having an elongated tubular wall defining an elongated lumen, and a distal opening in such wall at or near a distal end of the catheter, such opening being enveloped by an inflatable balloon;
inflating the balloon once the catheter is in proper position; and
advancing through the lumen and out through the distal opening into the balloon an elongated, pre-shaped ultrasound catheter having ultrasound transducer means carried near its distal end, allowing the ultrasound catheter to regain its pre-shaped configuration in the balloon to locate the transducer means closer to the wall of the passageway or cavity than the catheter lumen.

* * * * *